US00PP09993P

United States Patent [19]

Lamb et al.

[11] Patent Number: Plant 9,993

[45] Date of Patent: Aug. 5, 1997

[54] AGLAONEMA PLANT NAMED 'PENNY'

[75] Inventors: Ann E. Lamb, Sebring; Richard J. Button, Miami, both of Fla.

[73] Assignee: Sunshine Foliage World, Zolfo Springs, Fla.

[21] Appl. No.: 614,627

[22] Filed: Mar. 13, 1996

[51] Int. Cl.[6] ..... A01H 5/00

[52] U.S. Cl. ..... Plt./88.1

[58] Field of Search ..... Plt./88.1

*Primary Examiner*—James R. Feyrer

*Attorney, Agent, or Firm*—Foley & Lardner

[57] ABSTRACT

A new and distinct cultivar of Aglaonema named 'Penny' characterized by its distinctive broad, medium green leaves marked with silver-green, its dark bronze-green petioles, and its medium to large growth habit.

2 Drawing Sheets

The present invention comprises a new and distinct cultivar of Aglaonema, botanically known as *Aglaonema hybrida,* and referred to by the cultivar name 'Penny'.

The new cultivar is a product of a planned breeding program carried out by the inventor named J. Button in Miami, Fla. The new cultivar is a product of a cross of the following parentage:

Seed parent: Aglaonema 'Manilla Green Giant'
Pollen parent: Aglaonema 'Round Leaf'.

Asexual propagation by tissue culture and division beginning in February, 1989 and performed by, or under the supervision of, inventor Ann E. Lamb in Sebring, Fla. was used to increase the number of plants for evaluation and has demonstrated the stability of the combination of characteristics from generation to generation.

The following observations, measurements and values describe plants grown in Zolfo Springs, Fla. under shadehouse conditions which closely approximate those generally used in horticulture practice.

The following traits have been repeatedly observed to be characteristics which in combination distinguish 'Penny' from other Aglaonema of the same general type, for example, the cultivar 'Rembrandt', disclosed in U.S. Plant Pat. No. 7,440, and to which comparative reference is made.

1. The leaves of 'Penny' are distinctively broad and round compared to those of 'Rembrandt'.

2. Plants of 'Penny' grow larger and taller than 'Rembrandt' when grown under similar conditions.

3. The leaves of 'Penny' have green midribs and dark bronze-green petioles. Leaves of 'Rembrandt' have yellow marked midribs and pink petioles.

4. Plants of 'Penny' develop branches which emerge from the soil far from the main shoot, giving the plant a spreading growth habit. 'Rembrandt' develops branches which tend to emerge from the soil closer to the main shoot.

5. Plants of 'Penny' show little foliar damage when exposed to temperature of 43F for approximately 5 hours.

All color references are measured against The Royal Horticultural Society Colour Chart. Colors are approximately as color depends on horticultural practices such as light level and fertilization rate, among others, without, however any variances in genotype.

The drawings comprise a color photograph and a color photocopy, with the photo on Sheet 1 being a top perspective view of 'Penny', and the photocopy on Sheet 2 showing the detail of the color pattern on the upper side of an actual mature leaf of 'Penny'. The photograph on sheet 1 is of a plant of Penny in a 26 cm pot approximately 18 months after planting a single 4 leaf cutting and grown under appropriate growing conditions. Colors are as accurate as possible with color illustrations of this type.

Origin: Seedling selected from a cross of seed parent 'Manilla Green Giant' and pollen parent 'Round Leaf'.

Classification: *Aglaonema hybrida*, cv. 'Penny'.

Propagation: Asexual propagation either by division or tissue culture.

Plant: When cutting is grown in a 26 cm pot for 18 months under appropriate growing conditions, 'Penny' is approximately 14 cm to 16 cm from the soil surface to the junction of the petioles of the last two (2) unrolled leaves, and approximately 98 cm to 104 cm in width.

Stem:

*Growth pattern.*—The stem is upright in growth and approximately 1.5 cm to 1.8 cm in diameter five (5) cm above the soil surface. Internode distance is approximately 1.2 cm to 1.55 cm three (3) cm above the soil.

*Color.*—Darker and greener than, but closest to 199A.

Petiole: The following information is based on the 4th expanded leaf from the apex.

*Growth Pattern.*—The petiole has fleshy edges extending from the midrib and which are referred to as wings. The wings are approximately 4 mm to 6 mm wide one-half the distance from the petiole base to the wing apex. The wings extend from the base of the petiole to within approximately 7.1 cm to 12 cm of the base of the leaf. The apex of the wings is rounded. The petiole follows the stem axis but diverges from the axis approximately 19 cm to 20.5 cm from the leaf base, forming a horizontal distance from the vertical axis to the leaf base of approximately 7.8 cm to 10.2 cm.

*Dimensions.*—The petiole is straight from its base to the tip of the wings, and distinctly curved outward between the tip of the wings and the base of the leaf. The petiole is approximately 6 mm to 8 mm in diameter one-half the distance between the top of the wing and the base of the leaf. The petiole is approximately 23.8 cm to 27 cm in length.

*Color.*—The petiole wings and the midrib are 119A-B, tinged with greyed-orange lighter than but closest to 165A; wings and midrib become 147A, 148A with age.

Leaf:

*Growth pattern.*—The leaf is broadly ovate with a short cuspidate apex and a cordate base. The margin is entire. The leaf is asymmetric with the side of the leaf unrolling first having less surface area than the side unrolling last. The leaf is oriented parallel to the stem axis at the time of full unrolling, changing to approximately 60 degrees from the stem axis as more leaves unroll above it. The midrib is curved. The leaf blade is slightly wavy from the midrib to the margin, and often somewhat puckered between the primary veins.

*Dimensions.*—For the pot size and growing time indicated, the largest leaves are approximately 24.5 cm to 27.7 cm long and approximately 14.5 cm to 15.5 cm wide. Average sized leaves are approximately 21.4 cm to 23.4 cm long and approximately 13.5 cm to 14.8 cm wide. The leaf is moderately thick.

*Midrib.*—The midrib is thick and prominent, recessed on the upper leaf surface and protruding from the lower surface.

*Primary veins.*—The primary veins are sunken into the upper side and protrude slightly from of the underside. The primary veins are the same color as the tissue surrounding them.

*Pattern.*—The upper leaf surface are medium green, with large prominent silver-green chevrons following the primary veins are often coalescing into larger silver blotches. The midrib is green. The lower surface is entirely medium green.

*Colors.*—Mature leaf: Upper Surface: Medium green areas are 137B, silver green chevrons are 148C, 194C, and midrib is 137B-C. Lower surface is 146B-C, midrib 146D. Newly opened leaf: Upper surface: Medium green areas are shiny and greener than, but closest to 137C; silver green chevron areas are 194B; midrib —146C. Lower Surface: 146C-D, midribs 146C, lightly tinged with 199A.

*Axillary breaks.*—There are approximately 14 axillary branches with at least one leaf expanded. the branches tend to emerge from the soil far from the main shoot. The branches grow horizontally like a rhizome until they reach the side of the pot, at which they turn upward and emerge vertically from the soil. Leaves will show true color and pattern by the first leaf.

*Inflorescence.*—Typical of Aglaonema and does not have commercial significance.

Roots: Thick white roots with fine laterals.

General Observation

'Penny' is a medium to large growing Aglaonema having distinctive broad, rounded, medium green leaves prominently marked with silver-green chevrons and blotches. The petioles are dark bronze-green. These combined characteristics make 'Penny' a unique new cultivar.

We claim:

1. A new and distinct cultivar of Aglaonema plant named 'Penny', as illustrated and described.

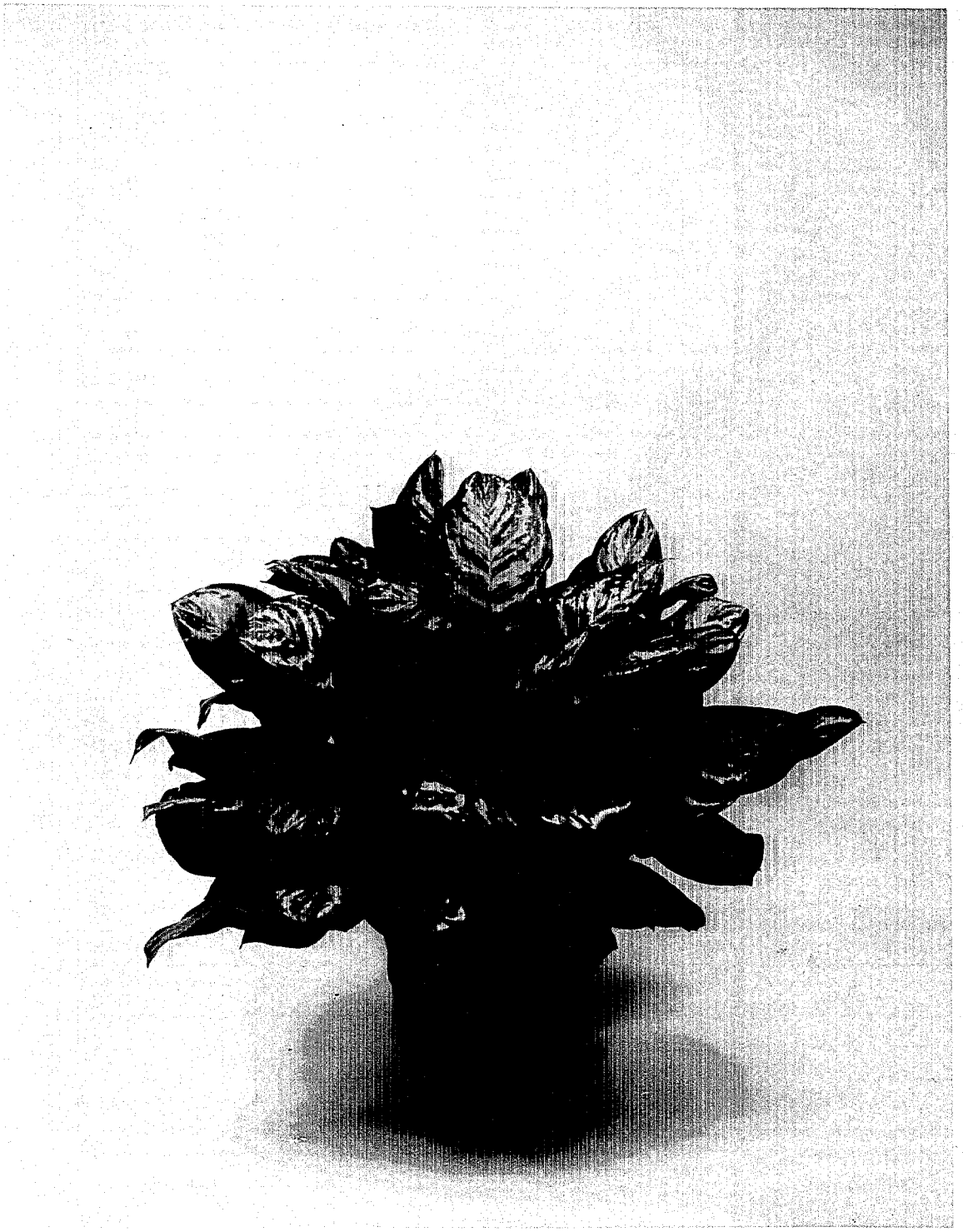

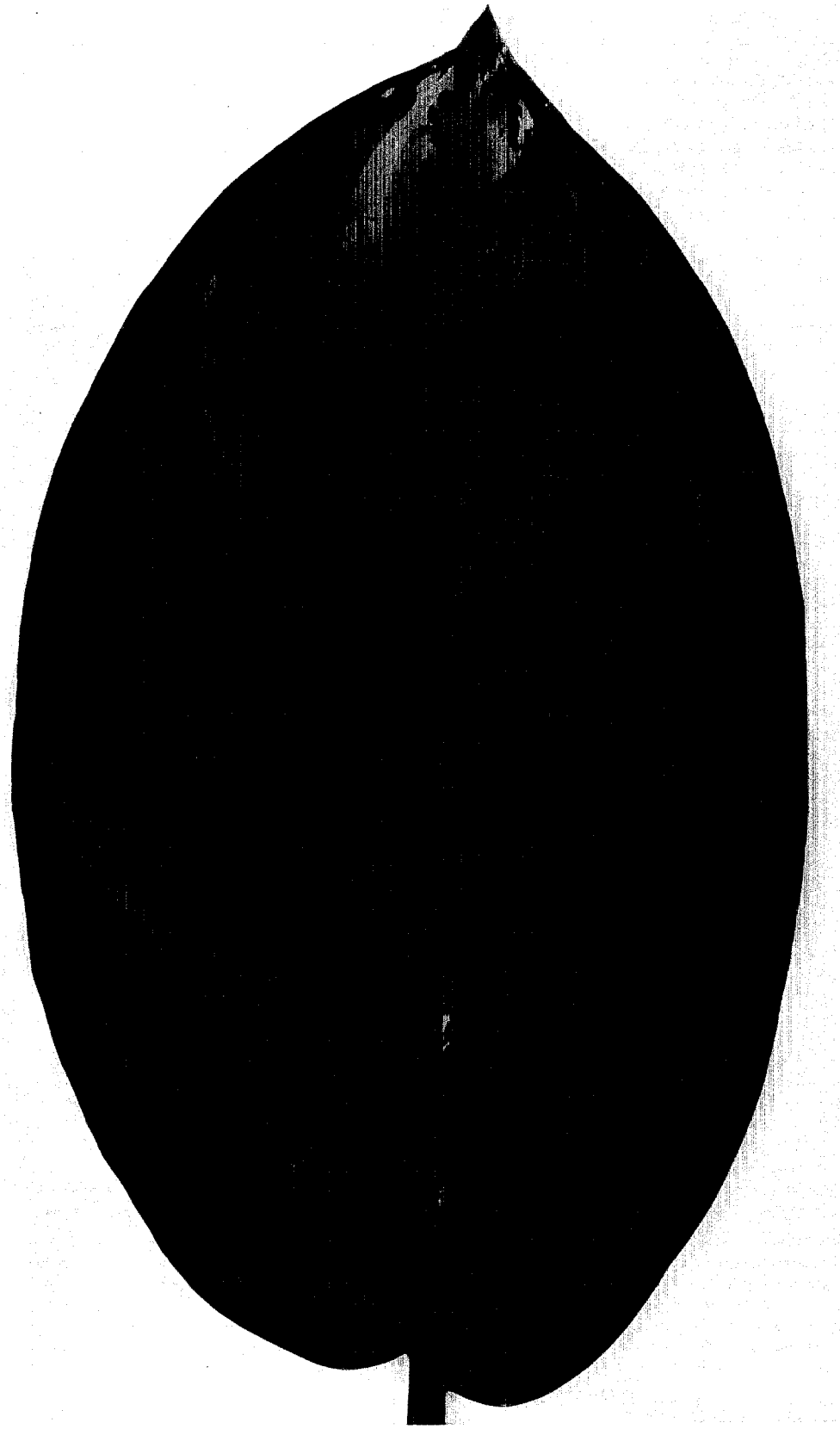

* * * * *